United States Patent [19]

Neracher

[11] Patent Number: 5,135,482
[45] Date of Patent: Aug. 4, 1992

[54] HYDRODYNAMIC DEVICE FOR THE ELIMINATION OF AN ORGANIC DEPOSIT OBSTRUCTING A VESSEL OF A HUMAN BODY

[76] Inventor: Arnold Neracher, 31,chemin du Nant d'Aisy, 1247 Anieres, Switzerland

[21] Appl. No.: 363,620

[22] Filed: Jun. 8, 1989

Related U.S. Application Data

[63] Continuation of Ser. No. 165,374, Feb. 29, 1988, abandoned, which is a continuation of Ser. No. 947,619, Dec. 30, 1986, abandoned.

[30] Foreign Application Priority Data

Dec. 31, 1985 [CH] Switzerland ............. 00055/86
Aug. 30, 1986 [CH] Switzerland ............. 03466/86

[51] Int. Cl.⁵ ................................ A61B 17/22
[52] U.S. Cl. ............................ 604/22; 606/128; 606/159
[58] Field of Search .......... 604/22; 606/159, 127, 606/128, 190

[56] References Cited

FOREIGN PATENT DOCUMENTS 3019115 12/1981 Fed. Rep. of Germany ... 128/303 R
3421390 12/1985 Fed. Rep. of Germany ...... 128/305
234608 4/1986 German Democratic Rep. ...................... 128/305

*Primary Examiner*—Michael H. Thaler
*Attorney, Agent, or Firm*—Robert E. Burns; Emmanuel J. Lobato

[57] ABSTRACT

A device and method for removal of organic deposit obstructions in blood vessels by use of a supersonic microjet liquid flow for canalizing the organic deposit obstruction to be removed. The device has a bendable tube insertable into a blood vessel in which an obstruction is to be removed. Within the tube extends a pressure-resistant duct having an outlet or nozzle orifice developed therein by a liquid under pressure provided from a pump. A small collapsable balloon, when inflated, centers the outlet and isolates a volume within the blood vessel upstream of the outlet for containing the microjet fluid and matter from the obstruction eroded and abraded from the deposit during canalizing. The volume is evacuated by a suction on the tube taken by a pump and the small balloon is inflated through the bendable tube with which it communicates.

8 Claims, 6 Drawing Sheets

HYDRODYNAMIC DEVICE FOR THE ELIMINATION OF AN ORGANIC DEPOSIT OBSTRUCTING A VESSEL OF A HUMAN BODY

This is a continuation of application Ser. No. 07/165,374, filed Feb. 29, 1988 now abandoned, which is a continuation of application Ser. No. 06/947,619 filed Dec. 30, 1986, now abandoned.

The present invention relates to a hydrodynamic device for eliminating an organic deposit partially or completely obstructing a vessel of the human body, consisting of a catheter having a flexible hose designed to be engaged in the obstructed vessel, a nozzle adapted to come proximate to the deposit to be removed, a pressurized liquid source feeding the nozzle through a flexible pressure-resistant duct extending in said hose, the stream formed by this nozzle being directed toward the deposit to be eliminated. This device is characterized by the fact that the nozzle bore defines a diameter comprised between 20 and 70$\mu$ (a micron equals $10^{-6}$ meters) and that the liquid pressure upstream of this bore is at least $6 \times 10^7$ Pa, one Pascal unit equals $10^{-5}$ bar). in such a way that the stream forcibly flowing from the nozzle penetrates the organic liquid contained in the vessel at an initial speed of at least 300 m/sec. The main advantages of the device relative to known devices are the following:

1. A clear cut of the deposit, without affecting the vessel wall together with incision and perforation without ablation of matter;
2. improved selectivity between the vessel wall and the deposit through direction and intensity control of the liquid jet;
3. possibility to operate in cut/incision/perforation mode without removal of matter if the jet speed is below Mach one at the nozzle outlet; the jet/matter interaction is then in the form of an elastic impact;
4. possibility to operate in removal/ablation/shear-stripping mode if the jet speed is equal to or higher than Mach one at the nozzle outlet; the jet/matter interaction is then in the form of a smooth impact, the jet kinetic energy being transformed in heat and pressure (thermo-dynamic effect). The effects of temperature increase are much circumscribed because heat is intantaneously evacuated by the jet itself.
5. Through use of a pulsed jet, possibility to combine the cut/ablation effects thanks to the transitory effect of the jet speed. This jet speed is dependent upon the input pressure of the nozzle.

The annexed drawing shows, schematically and as an example, several embodiments of the invention.

Figure 1:
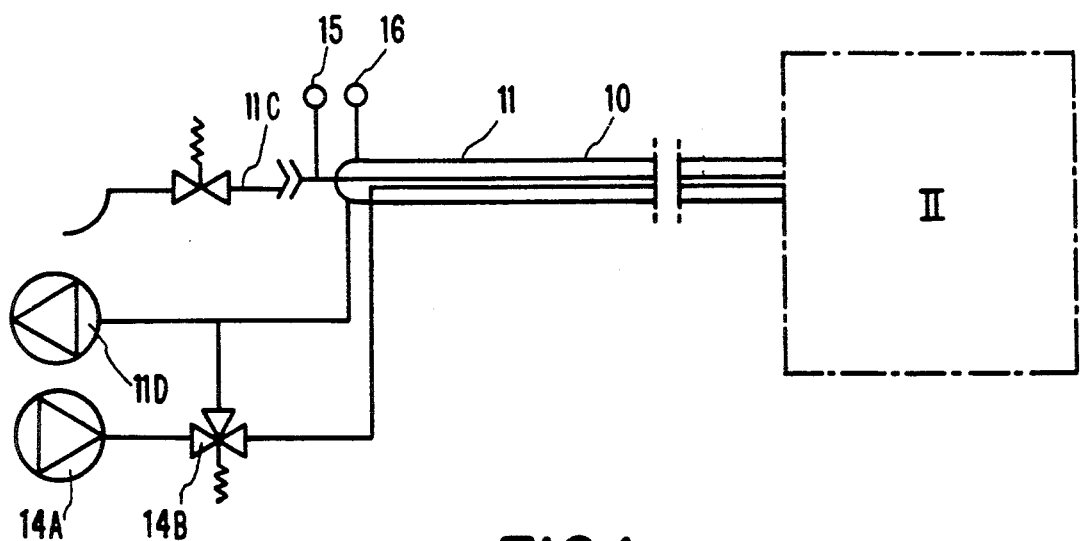
FIG. 1 is a schematic view of a first embodiment of the invention.
Figure 2:
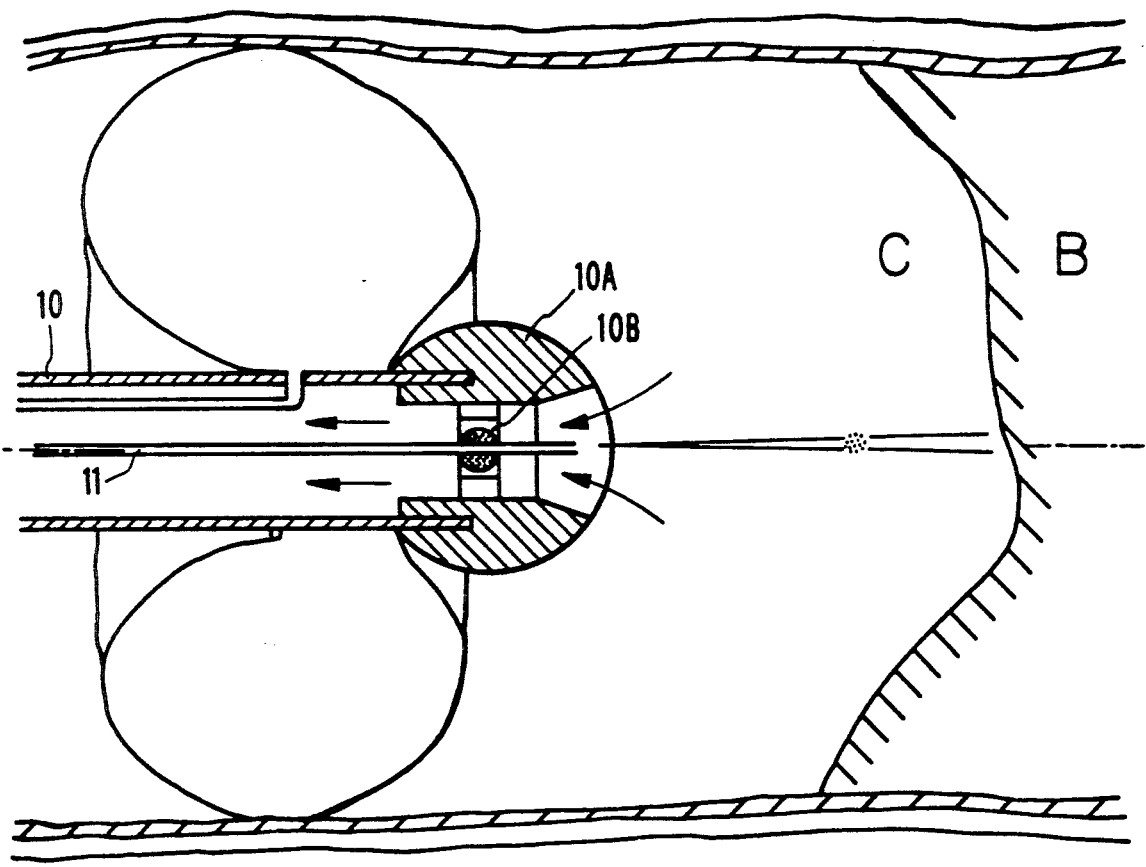
FIG. 2 is a longitudinal sectional view, on an enlarged scale of the end of the device appearing in the right-hand side box, in dotted lines, of FIG. 1.

The embodiment shown in FIGS. 1-2 comprises a catheter consisting of a flexible hose 10, made of synthetic material, a flexible pressure-resistant duct 11, made for example of a ductile metal or of a prestressed insulating material, such as a polycarbonate reinforced with KEVLAR fibers and characterized by good flexibility and capability to withstand internal pressures of the order of $2 \times 10^8$ Pa and extending within the hose 10, a high pressure pump 12, a nozzle 13 secured to the end of duct 11 by welding or gluing, an inflatable small balloon 14, two handles 15 and 16 permitting axial and angular displacement of hose 10 and duct 11 in independent manner. The pump 12 feeds the duct 11 with a high pressure liquid via a line 11A, a pressure regulator 11B, and a quick coupling 11C. When regulator 11B is operating, nozzle 13 is fed with high pressure liquid and sprays a supersonic jet (approximately in the axis of vessel A, toward deposit B).

The small balloon 14 insures centering of the nozzle 13 in the vessel and prevents the liquid of the jet from flowing back through the vessel. The small balloon 14 is inflated by a pump 14A provided with a pressure regulator 14B via a hose 14C.

To displace nozzle 13 forwardly during the elimination of the deposit, handles 15 and 16 are used. The end of hose 10 is provided with a spherical body 10A, having an axial passageway in which is carried a ball-and-socket joint 10B through which extends duct 11, allowing to incline the jet C up to 10 degrees relative to the vessel axis.

The above-described device operates as follows: after the catheter has been engaged in the vessel and has been displaced therein, concurrently with the duct 11, by using handles 15 and 16 until the nozzle 13 comes near deposit B and is suitably oriented, the pump 12 is started and the regulator 11B is adjusted, so that the jet C reaches a supersonic speed. This jet strikes deposit B and destroys it, dismantles it, or disintegrates it, depending on the jet speed and on the type of nozzle used, through cutting, incision, ablation, shear-stripping or perforation.

The liquid filling up space D is evacuated together with the deposit matter through the body 10A and the hose 11 under the action of a pump 11D connected to hose 11.

To obtain a supersonic jet having the following features:

$P = 10^8$ Pa
speed = 300 m/s
flow = $10^{-6}$ m$^3$/s
E kin = 45 Joules/s one should advantageously use: a metal duct 10 of steel-type 316 L, with an internal diameter of $2 \times 10^{-4}$ m; and of external diameter of $3 \times 10^{-4}$ m; a nozzle 13 of internal diameter = $6 \times 10^{-5}$ m, and of external diameter = $3 \times 10^{-4}$ m.

The embodiments of the invention shown in FIGS. 3 to 12 have been designed and constructed in view of solving the technological problem created by the very high pressure, higher than $6 \times 10^7$ Pa, 13 which has to be sustained by nozzle 13, and the extremely small diameter of its bore comprised between 20 and 70μ. To solve this problem, the nozzles 13 of these various embodiments are formed, at least in part, by the end of duct 11. The device shown in FIGS. 3–4 comprises a catheter consisting of a flexible hose 10, in plastic material, a flexible metallic duct 11 extending within hose 10, a high pressure liquid source 12, a nozzle 13, an inflatable small balloon 14 integral with hose 10, two handles 15 and 16 allowing axial and angular displacement of hose 10 and duct 11, in an independent fashion, and a radio opaque collar 17 mounted at the end of hose 10.

Passageway 18, which is constituted by the bore of hose 10, and a channel 19, provided in the thickness of the wall thereof and opening in the small balloon 14, are adapted to be connected at 20 and 21, respectively, to a vacuum pump and to a pressurized fluid source.

Duct 11, constructed from stainless steel or from a rust-proof alloy, has an exterior diameter of 0.3 mm and an interior diameter of 0.2 mm. It has a burst-resistance of about 2200 N/mm².

Nozzle 13 is made exclusively from the end of duct 11 which is formed of two sections: a first section of length $L_A$, the bore cross-section of which continuously decreases, and a second section, of length $L_B$ of constant bore cross-sectional area. Length $L_A$ is equal to about 800μ, length $L_B$ to about 160, and the diameter of outlet 22 is 40μ.

Angle α is 15° and the ratio between the bore cross-sectional area of duct 11 and of outlet 22 is about 100. The outlet modulus ψ, appearing in the relation $$V = \psi \sqrt{2gH}$$

where H defines the liquid pressure upstream from the nozzle, and where V is equal to the jet speed in the plane of bore 22, is equal to 0,98 for the nozzle.

For a pressure of $6 \times 10^7$ Pa, the jet speed is 350 m/sec. This speed reaches 60 m/sec. for a pressure of $2 \times 10^8$ Pa. The supersonic jet injected in the organic liquid contained in vessel A is formed of a needle-like shape portion, which is much tapered and extremely incisive, and of a surrounding, incoherent turbulent portion 24. The length of needle-shape portion 23 is about equal to 5 to 50 times the diameter of outlet 22.

The device is to be used as follows:

A hose 10 is engaged in the vessel A clogged by a deposit B until the collar 17 comes in immediate proximity to this deposit to be eliminated, then the small balloon 14 is inflated by a fluid entering at 21; duct 11 is then engaged in hose 10 until the nozzle reaches the level of collar 17. Duct 11 is fed with pressurized liquid, so that the needle-shape portion 23 of the supersonic jet attacks deposit B according to a well-defined impact zone and begins the destruction thereof.

Handle 16 can be manipulated so as to displace nozzle 13 axially and angularly, whereby the latter can be most effective against the deposit. In order to control in the best possible way the changes in position and orientation of the jet and, more particularly, the needle-shape jet portion 23, as well as to ascertain de visu, in real time, the evolution of the deposit elimination, a liquid containing an X-ray contrasting product will be advantageously used.

Figure 5:
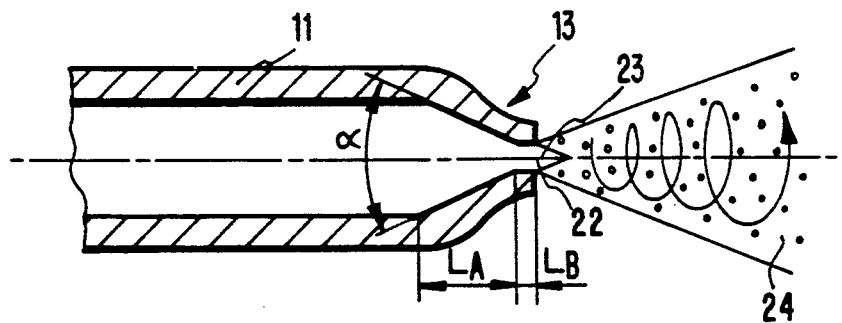
FIGS. 5 to 10 are views similar to that of FIG. 4 of nozzles of six other embodiments of the invention having substantially the same overall structure of the device shown in FIG. 3.

The liquid carrying the fragments from the fractioned deposit is sucked back by a vacuum pump connected at 20 and evacuated outwardly through passageway 18. It is to be noted that the action of needle-shape jet portion 23 may be worked out, depending on its features, by ablation, incision, erosion, cutting, etc. The nozzle 13 shown in FIG. 5 is exclusively constituted from the end of metal duct 11 and forms two bore sections, as for the nozzle of FIG. 4. The first section of length $L_A$ is frusto-conical, and the second section of length $L_B$ is cylindrical. The diameter of the second bore section is 70 μ and angle α of the first bore section is equal to 60°.

Length $L_A$ is approximately equal to the inner diameter of duct 11 and the length $L_B$ is smaller than or equal to half the diameter of outlet 22. The outlet modulus ψ of this nozzle is equal to 0.8. For an input pressure of about $10^8$ Pa, the needle-like jet portion 23 extends over a length of about 2 to 10 times the diameter of outlet 22. It is surrounded by a turbulent area 24, the turbulency being created by the roughness of the internal wall of the cylindrical bore section. This turbulency itself generates a whirlpool facilitating a cavitation action. Duct 11 is made of stainless steel and its end is tempered.

Figure 6:
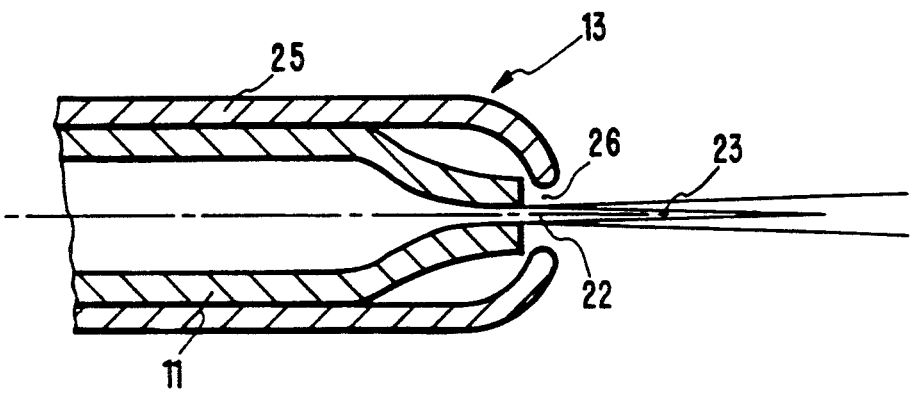

The nozzle 13 of FIG. 6 is adapted to be fed by a liquid under relatively high pressure, of the order of 3 to $15 \times 10^8$ Pa. It is constituted by two elements: the end of the flexible metallic duct 11 and the end of a surrounding friction-fit tube 25 extending over all the length of duct 11.

These two elements are constructed from metallic alloys, having respective burst resistances of about 2000 N/mm² and 2700 N/mm².

Tube 25 is rounded proximate its opening 26 to prevent any shearing action against the vessel wall and the diameter of this opening is about twice that of outlet 22. With a liquid pressure in the order of $15 \times 10^8$ Pa, the supersonic jet speed may reach 1700 m/sec., which represents, for a diameter of 40μ of outlet 22, a flow of 2 cm³/sec. and a power output of about 2 KW.

To take into account the not negligeable calorific energy dissipated by this nozzle, working conditions should be discontinuous.

Figure 7:
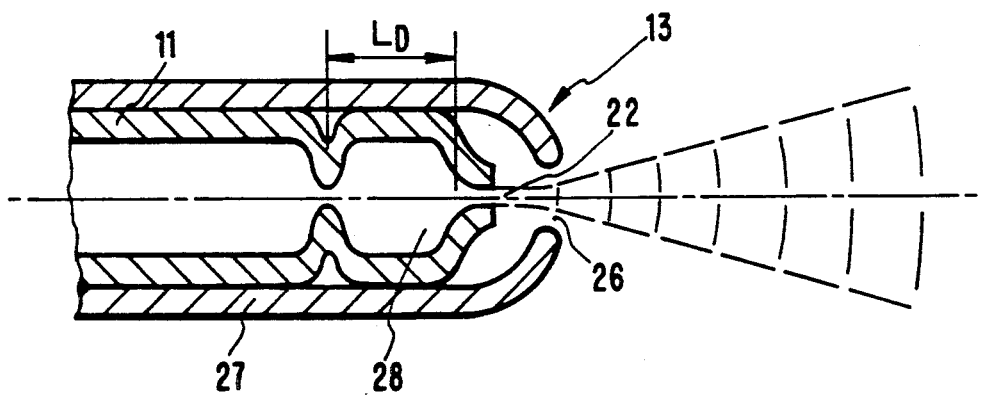
Figure 8:
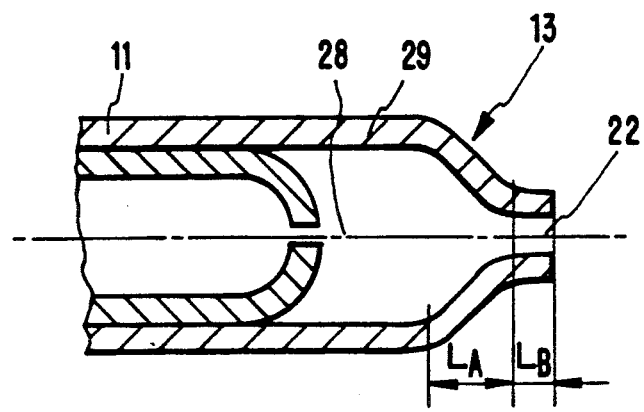

The nozzle 13 shown in FIG. 7 is also constituted of two elements: the end of metallic duct 11 and the end of a shielding sheath 27, of metallic or plastic material. This nozzle 13 defines a resonance chamber or resonant cavity 28, formed by a narrowing of duct 11. The liquid comes upstream from this chamber 28 at a relatively low constant pressure, of about $6 \times 10^7$ Pa, and exits by outlet 22 at a speed which periodically changes. The frequency of these changes depends on the length $L_D$ of the chamber 28 and on the propagation speed of the elastic wave in the liquid. The variable speed supersonic jet of this nozzle is particularly favorable for the elimination of hard organic deposits. The nozzle shown in FIG. 8 is a variant of that shown in FIG. 7.

Figure 9:
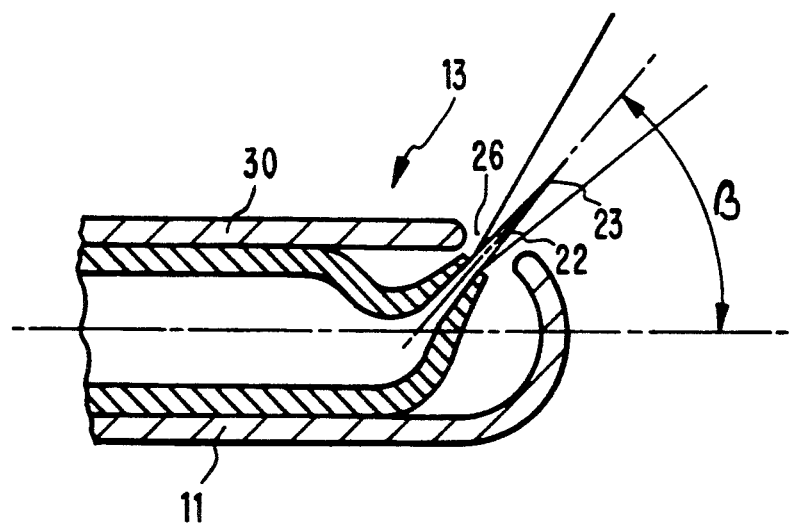

It is constituted by the end of a flexible metallic duct 11 and by the end of a surrounding friction-fit, metallic tube 29. These ends are longitudinally offset so as to define a resonance chamber 28 therebetween. The outlet 22 of this nozzle 13 is constituted by the opening of the friction-fit tube 29. The end of that tube 29 includes a frusto-conical bore section of length $L_A$ and a cylindrical bore section of length $L_B$ which approximately corresponds to the respective lengths of the bore sections of nozzle 13 shown in FIG. 5. The nozzle shown in FIG. 9 is a variant of the one shown in FIG. 6.

It is constituted by the end of a metallic duct 11 and by the end of a shielding tube 30 made in metal or plastic material. The end of duct 11 is elbowed in such a way that the axis of the cylindrical bore section and of the outlet 22 forms an angle β of 60° with the axis of vessel A.

Alternately, this angle β could be different from 60° and could be comprised between 0° and 120°.

Curved edge opening 26 of tube 30 is positioned in register with outlet 22.

Figure 10:
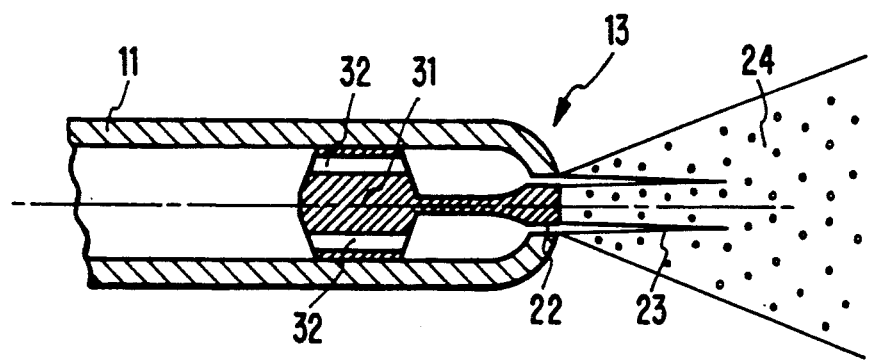

Nozzle 13 shown in FIG. 10 is constituted by the end of metallic duct 11 and by a metallic part 31 mounted interiorly of duct 11. This part 31 comprises passageways 32 for the liquid and an extension ending interiorly of outlet 22.

The supersonic jet produced by this nozzle is made of an annular needle-like portion 23 and of a surrounding zone containing micro-bubbles inducing a very important cavitating action on the deposit. The average speed of this jet is about 100 to 400 m/sec.

Figure 11:
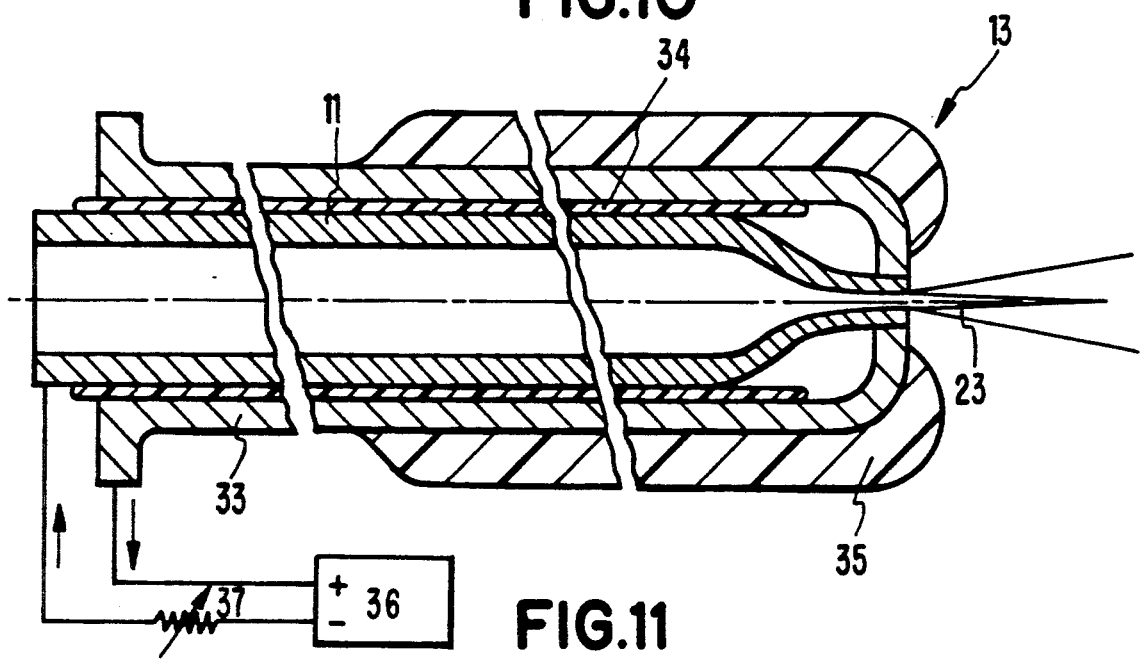
FIG. 11 is a longitudinal section of another embodiment of the invention, comprising a so-called >memory-shape< nozzle.

The device shown in FIG. 11 comprises a nozzle 13, of the so-called memorized-shape type, being characterized by its capacity to orient itself in various determined positions as a function of variations in the temperature.

This nozzle 13 is constituted by several elements: the end of metal duct 11 and an exterior tube 33 constructed in a memorized-shape type of alloy of the titanium-aluminum type, a tube 34 made of electrically-insulating material mounted between the end of duct 11 and the tube 33, and a peripheral tube 35, made of a thermally-insulating material. Duct 11 and tube 33 are electrically inter-connected at their ends. An electrical generator 36, of constant voltage type, and a variable resistance 37, allow an electric current of variable intensity to circulate in these elements and to thus modify their temperature. Suitably-monitored temperature changes yield predetermined orientation changes of the nozzle 13 and, consequently, modifications of the supersonic jet direction.

Figure 3:
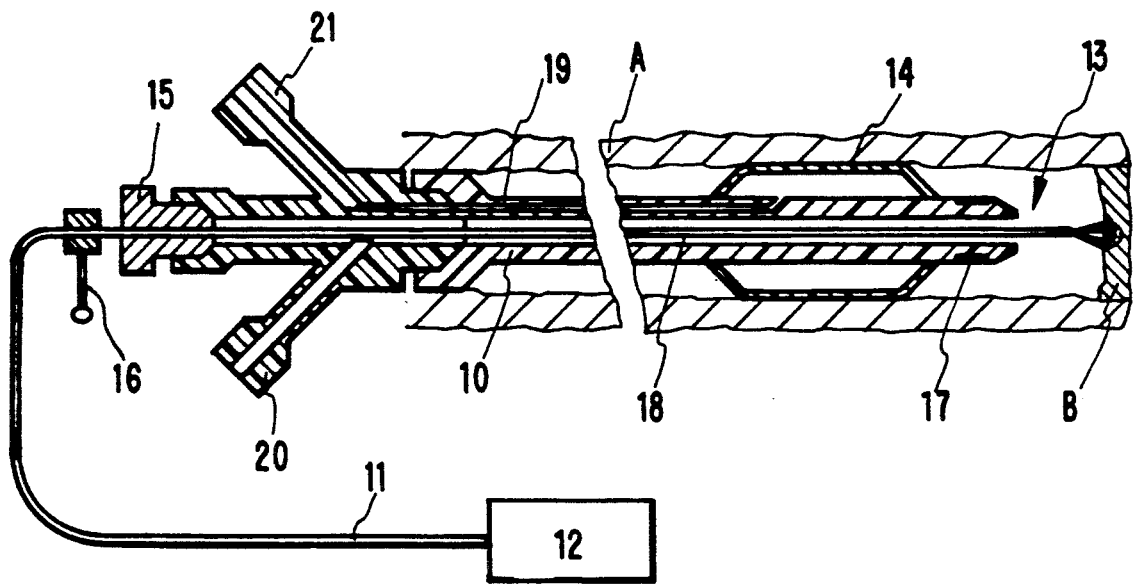
FIG. 3 is a longitudinal section of a second embodiment of the invention.
Figure 4:
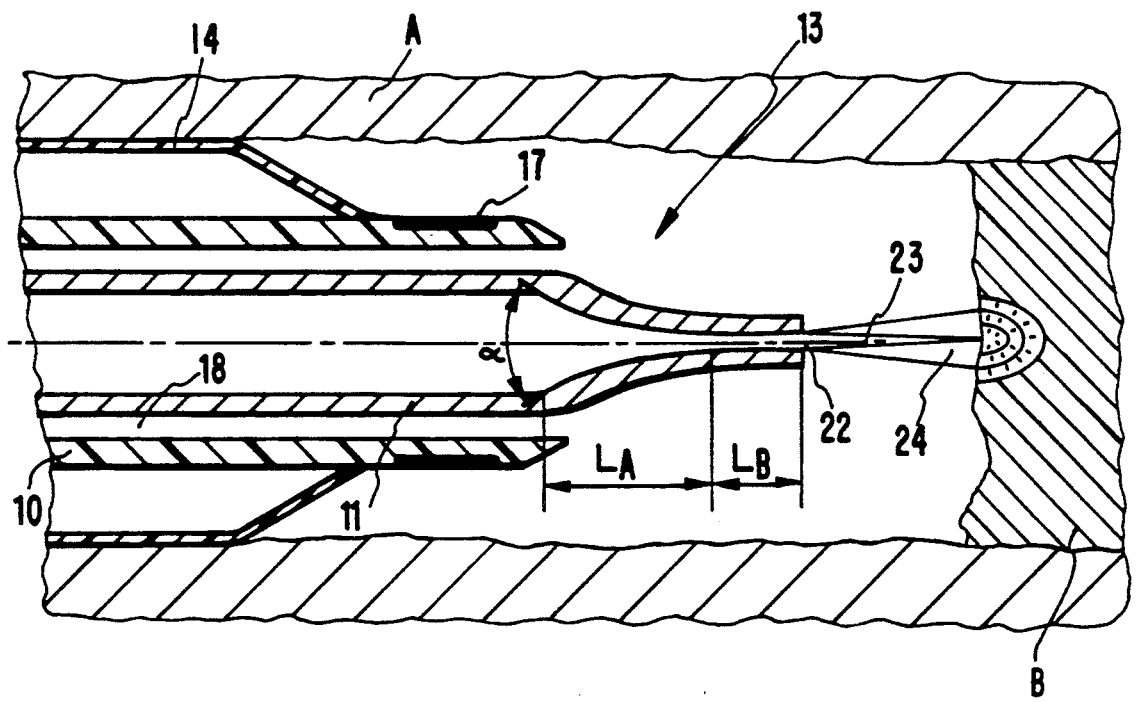
FIG. 4 is an enlarged, longitudinal section of the nozzle of the second embodiment.
Figure 12:
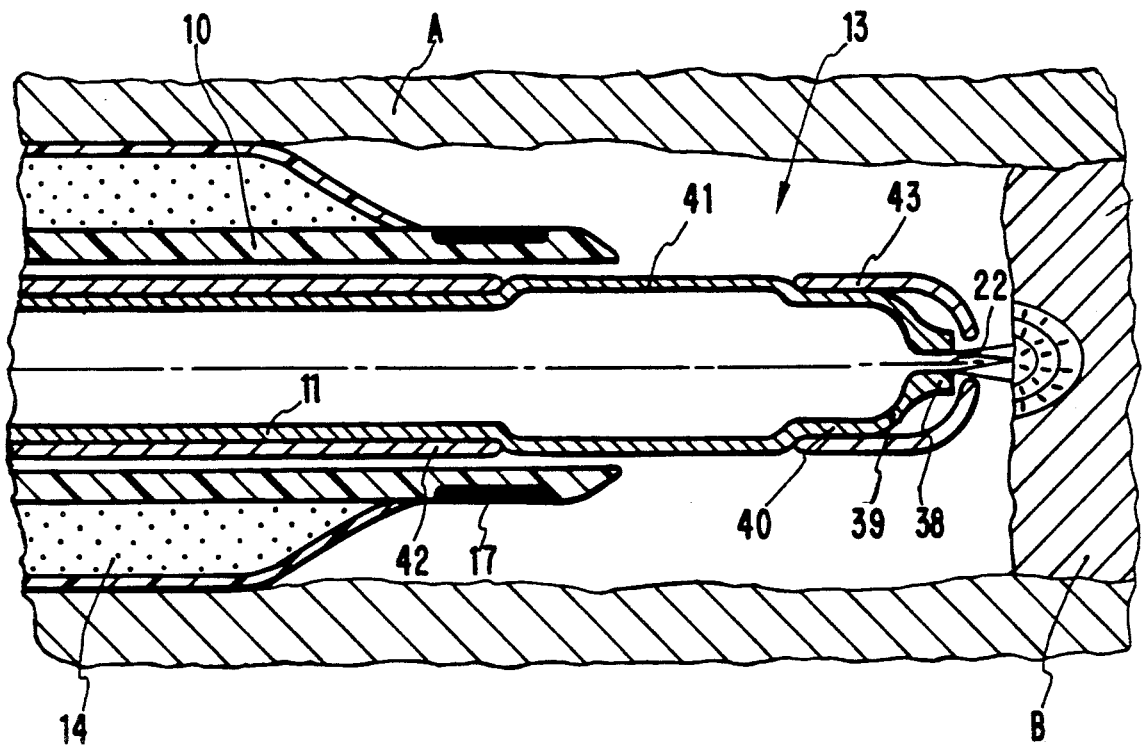
FIG. 12 is a longitudinal section of another embodiment of the invention, wherein the nozzle has an integral expandable small balloon.

The device shown in FIG. 12 is constituted by a catheter having as for the one in FIG. 3, a flexible hose 10, made of plastic material, an integral small balloon 14 and a radio-opaque collar 17, a flexible metallic duct 11 and a nozzle 13. Duct 11 is constructed from an alloy, the permanent deformation threshold of which is very high, and thus allows same to sustain lengthenings in the order of 500 to 700% of the initial value thereof.

The end of duct 11, which constitutes a part of nozzle 13, is formed of a cylindrical section 38, the opening of which constitutes the outlet 22 of the nozzle 13, a frusto-conical section 39 and cylindrical sections 40 and 41 of diameters equal to and slightly greater than that of duct 11 respectively.

Figure 13:
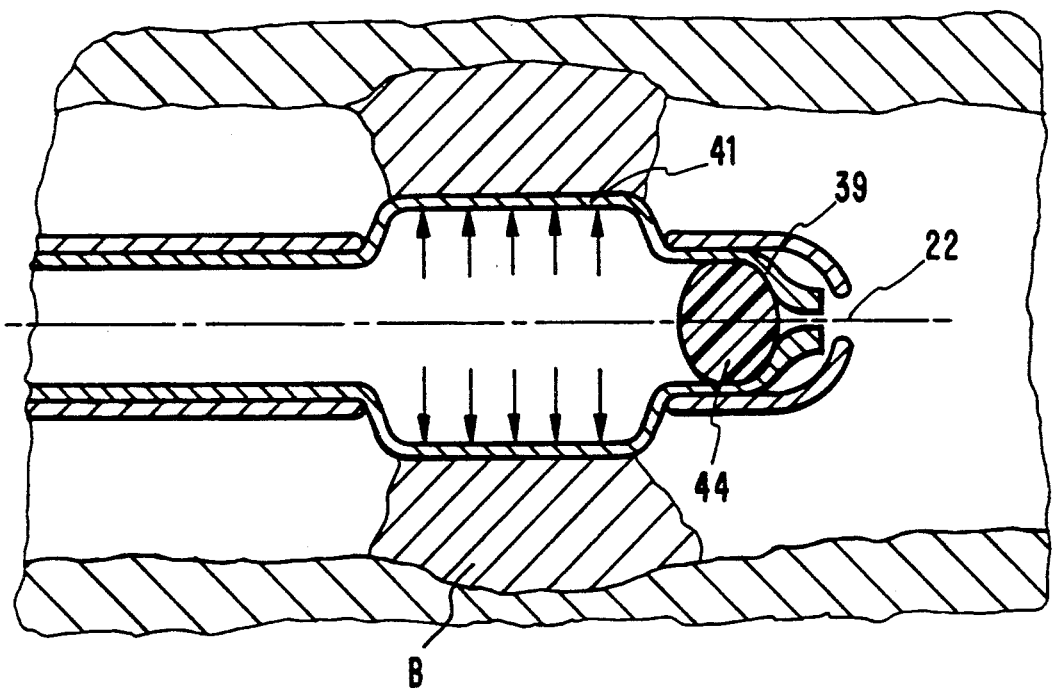
FIG. 13 is a view similar to that of FIG. 12, showing how this latter embodiment of the invention operates.
Figure 14:
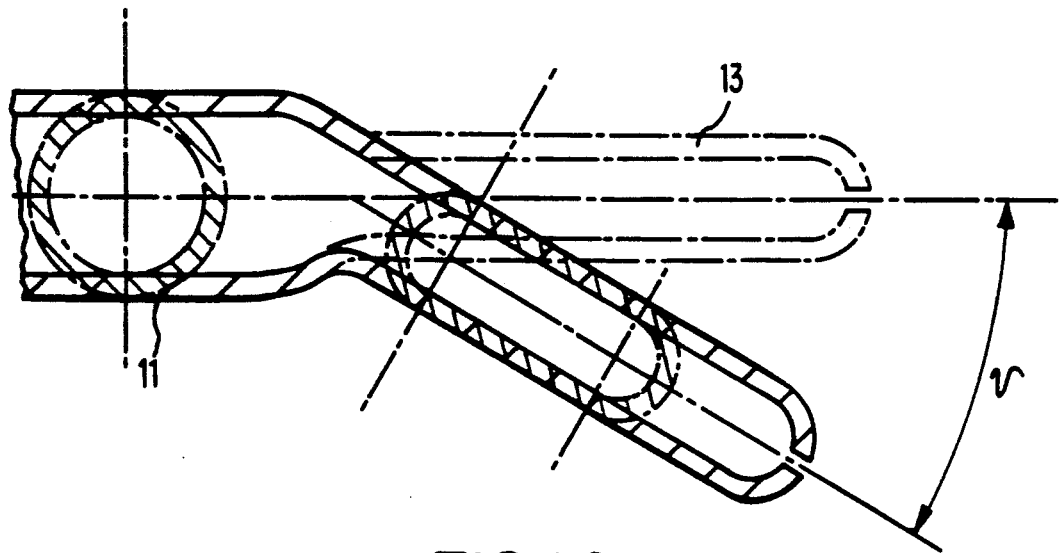
FIGS. 14 and 15 are views similar to that of FIG. 4, showing nozzles according to two additional embodiments of the invention having substantially the same overall structure of the device shown in FIG. 3.

Duct 11 is fitted up to section 41, within a friction-fit steel sheath 42 and the section 40 within friction-fit tip 43, made of steel and rounded at its end. The cylindrical section 41 is therefore free of any constraint. This device is used as follows: after having brought the end of hose 10 into clogged vessel A proximate the deposit B to be eliminated, the small balloon 14 is inflated, then the nozzle is put in place by displacing the duct 11 within the hose 10. The deposit is then attacked by the supersonic jet generated by the nozzle 13, by progressively moving into the deposit until it perforated from end to end. With this result, a plastic ball 44 (see FIG. 13) is introduced into the duct 11; this ball of a diameter equal to the interior diameter of section 40, so that this ball 44, carried by the liquid, the pressure of which has been reduced, comes to abut against the seat defined by the section 39 and to close the outlet 22. Then the liquid pressure is increased, so as to induce expansion of the section 41, which comes in contact with the wall surface of the deposit perforation. The expanded diameter of the section 41 may reach a value of the order of 0,6 to 1 mm, i.e. three times its initial diameter. This deposit perforation may be further enlarged, if deemed necessary, by withdrawing the nozzle 13 and by ending its dilatation through use of the small balloon 14. The nozzle shown in FIG. 14, the so-called Bourdon effect type of nozzle, distinguishes itself from the others in that the end section of duct 11 has been flattened and slightly curved, so as to define an elliptical cross-section as well as to form an angle ν with the axis of the duct.

When the liquid pressure feeding the nozzle increases, this angle ν decreases, since the end section is biased to straight position, and, inversely, so as to yield jet scanning and an increase of the deposit-impacting surface, through variations of the pressure between two limit values. The swept surface of the deposit is still increased by combining the Bourdon effect with axial rotation of the duct.

Figure 15:
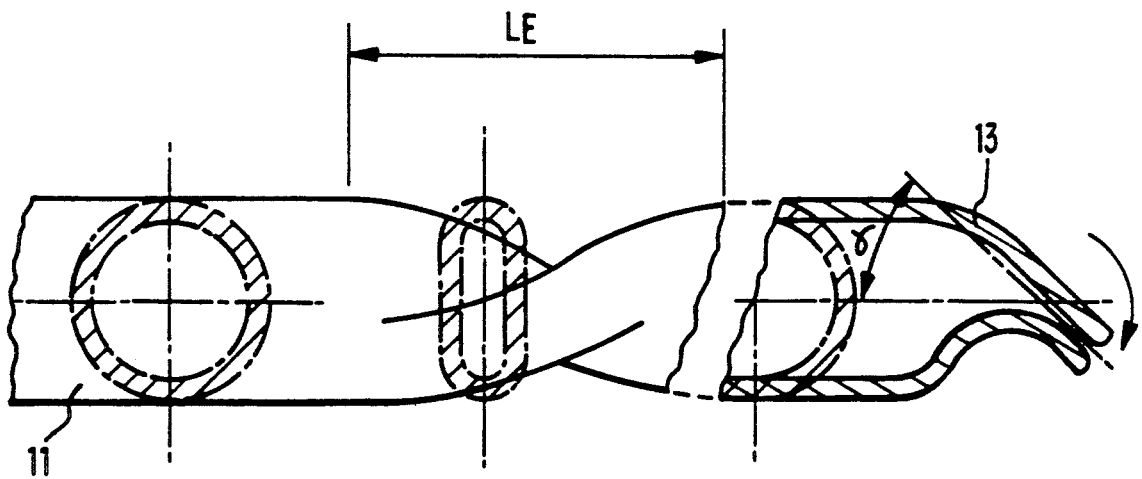

The nozzle shown in FIG. 15, or so-called spiral effect type of nozzle, distinguishes itself from the preceding ones in that the duct 11 has been flattened and twisted over part of its length, so that the corresponding section defines an elliptic cross-section as well as a spiral figure. Moreover, its circular end forms a predetermined angle with the axis of the duct 11. When the nozzle is fed with pressurized liquid, the spiral section straightens out and, consequently, the circular nozzle end rotates around the axis of the conduit. By varying the liquid pressure between two limit values, a circular and alternating scanning of the jet is obtained, whereby the impacting surface of the deposit is increased.

Amongst the numerous advantages of the described devices, the following are to be noted:

1) the sterilizing effect of the liquid constituting the jet because of the very high pressure variation in a very short time;

$$\frac{\Delta p}{\Delta t}$$

$\approx 10^{13}$ to $10^{14}$ Pa/sec.

2) very sensitive and very precise adjustment of the depth of action of the jet, as a function of the pressure and of the impacting duration;
3) real time vision via an X-ray camera of the evolution of the deposit elimination, thanks to the contrasting liquid;
4) a backward thrust on the nozzle of the order of 0,4N, corresponding to an average pressure of the order of 125 N/mm² at the level of the jet impact on the deposit;
5) a jet-impacting force which is proportional to the sinus of the impacting angle on the deposit, thus maximum at the level of the deposit and minimum at the level of the vessel wall;
6) real time operation by the use of X-ray contrasting which permits to visualize directly the cutting or eroding action of the jet during the intervention;
7) creation of a hole in the deposit large enough to allow insertion of the small balloon;

8) no thermal lesions since heat is evacuated by the liquid itself
9) the patient does not suffer from thermal action;
10) perforation risk is practically nil when the deposit is pierced from side to side (the so-called dechanelling effect);
11) possibility to use a probe or catheter assembly of a diameter as small as 0.15 mm and, therefore, capable of insertion into arteries of very small calibre.

The invention is of course not limited to the devices described and shown.

More particularly, the nozzle 13 could be constituted, as another embodiment of the invention, by the end of the duct 11 closed by a plug, this plug defining an aperture constituting the bore 22 of the nozzle 13.

Nozzles of this latter type could be substituted to nozzles shown in the drawing, without departing from the scope of the invention.

What I claim is:

1. A hydrodynamic device for the elimination of an organic deposit obstructing a vessel of a human body comprising,
    a flexible hose of synthetic material insertable in said vessel,
    a bendable pressure-resistant duct extending through said hose with an annular passageway between said duct and said hose, a rear end portion of said duct extending beyond a rear end of said hose,
    handle means on rear end portions of said hose and said duct respectively for moving said duct axially and angularly with respect to said hose,
    a collar of radio opaque material on a forward end of said hose,
    the forward end of said duct comprising a nozzle extending beyond the forward end of said hose,
    a balloon surrounding a forward portion of said hose rearward of said collar,
    a conduit, isolated from said annular passageway, leading from said balloon to a rearward portion of said hose,
    a source of high pressure liquid connected with a rear end of said duct,
    suction means connected with said passageway for withdrawing liquid from said vessel,
    a source of low pressure fluid connected with said conduit for inflating said balloon,
    means for regulating the pressure of said low pressure fluid and thereby regulating the inflation of said balloon,
    the bore of said nozzle having a diameter between 20 and 40 microns and said source of high pressure liquid providing a pressure of at least $6 \times 10^7$ Pa to produce a needle-shaped jet issuing from said nozzle at supersonic speed for penetrating and eroding said deposit.

2. A hydrodynamic device according to claim 1, in which said duct is of rust proof metal having an external diameter of about 0.3 mm and internal diameter of about 0.2 mm.

3. A hydrodynamic device according to claim 1, in which said nozzle has a first section in which the internal diameter continuously decreases and a second section of constant internal diameter.

4. A hydrodynamic device according to claim 1, in which said nozzle has a resonance chamber upstream of the nozzle orifice.

5. A hydrodynamic device according to claim 1, further comprising a spherical body on a forward end of said hose, said spherical body having a socket joint through which said duct extends for inclination of the jet in relation to the axis of said vessel.

6. A hydrodynamic device according to claim 1, in which the forward end of said duct is elbowed to direct a jet at an angle to the axis of said hose, said duct being rotatable in said hose by said handle on a rear end of said duct to direct the jet in different directions.

7. A hydrodynamic device for the elimination of an organic deposit obstructing a vessel of a human body comprising,
    a flexible hose of synthetic material insertable in said vessel,
    a bendable pressure-resistant duct extending through said hose with an annular passageway between said duct and said hose, a rear end portion of said duct extending beyond a rear end of said hose,
    handle means on rear end portions of said hose and said duct respectively for moving said duct axially and angularly with respect to said hose,
    a collar of radio opaque material on a forward end of said hose,
    a nozzle on the forward end of said duct extending beyond the forward end of said hose,
    a balloon surrounding a forward portion of said hose rearward of said collar,
    a channel leading from said balloon to a rearward portion of said hose,
    a source of high pressure liquid connected with a rear end of said duct,
    suction means connected with said passageway for withdrawing liquid from said vessel,
    a source of low pressure fluid connected with said channel for inflating said balloon,
    the bore of said nozzle having a diameter between 20 and 70 microns and said source of high pressure liquid providing a pressure sufficiently high to produce a needle-shaped jet of supersonic speed from said nozzle,
    a forward end portion of said duct being of a memory-shape type alloy and means being provided for electrically heating said forward end portion of said duct and thereby modifying the direction of the jet.

8. A hydrodynamic device for the elimination of an organic deposit obstructing a vessel of a human body comprising,
    a flexible hose of synthetic material insertable in said vessel,
    a bendable pressure-resistant duct extending through said hose with an annular passageway between said duct and said hose, a rear end portion of said duct extending beyond a rear end of said hose,
    handle means on rear end portions of said hose and said duct respectively for moving said duct axially and angularly with respect to said hose,
    a collar of radio opaque material on a forward end of said hose,
    a nozzle on the forward end of said duct extending beyond the forward end of said hose,
    a balloon surrounding a forward portion of said hose rearward of said collar,
    a channel leading from said balloon to a rearward portion of said hose,
    a source of high pressure liquid connected with a rear end of said duct,
    suction means connected with said passageway for withdrawing liquid from said vessel, a source of low pressure fluid connected with said channel for inflating said balloon, the bore of said nozzle having a diameter between 20 and 70 microns and said source of high pressure liquid providing a pressure sufficiently high to produce a needle-shaped jet of supersonic speed from said nozzle, a forward end portion of said duct being flattened and twisted and said nozzle being directed at an angle to the axis of said hose, and means being provided for varying the pressure of said high pressure liquid and thereby varying the degree to which said duct is straightened by liquid pressure.

* * * * *